United States Patent
Hu

(10) Patent No.: US 9,815,778 B1
(45) Date of Patent: Nov. 14, 2017

(54) CYCLIC PROCESS FOR PRODUCING TAURINE

(71) Applicant: VITAWORKS IP, LLC, North Brunswick, NJ (US)

(72) Inventor: Songzhou Hu, Princeton, NJ (US)

(73) Assignee: VITAWORKS IP, LLC, North Brunswick, NJ (US)

( * ) Notice: Subject to any disclaimer, the term of this patent is extended or adjusted under 35 U.S.C. 154(b) by 0 days.

(21) Appl. No.: 15/366,798

(22) Filed: Dec. 1, 2016

Related U.S. Application Data

(63) Continuation-in-part of application No. 15/268,071, filed on Sep. 16, 2016, now Pat. No. 9,745,258.

(51) Int. Cl.
C07C 303/02 (2006.01)
C07C 303/32 (2006.01)
C07C 303/44 (2006.01)

(52) U.S. Cl.
CPC .......... C07C 303/02 (2013.01); C07C 303/32 (2013.01); C07C 303/44 (2013.01)

(58) Field of Classification Search
CPC .... C07C 303/02; C07C 303/32; C07C 303/44
See application file for complete search history.

(56) References Cited

U.S. PATENT DOCUMENTS

| | | |
|---|---|---|
| 1,932,907 A | 10/1933 | Nicodemus |
| 1,999,614 A | 4/1935 | Nicodemus et al. |
| 2,693,488 A | 11/1954 | Sexton |
| 2,820,818 A | 1/1958 | Sexton |
| 5,646,320 A | 7/1997 | Cassady et al. |
| 5,739,365 A | 4/1998 | Briody et al. |
| 8,609,890 B1 | 12/2013 | Hu |
| 9,061,976 B1 | 6/2015 | Hu |
| 9,108,907 B1 | 8/2015 | Hu |
| 9,428,450 B2 | 8/2016 | Hu |
| 9,428,451 B2 | 8/2016 | Hu |
| 9,573,890 B2 | 2/2017 | Hu |

(Continued)

FOREIGN PATENT DOCUMENTS

| | | |
|---|---|---|
| CN | 101486669 A | 7/2009 |
| CN | 101508657 A | 8/2009 |

(Continued)

OTHER PUBLICATIONS

USPTO Non-Final Office Action dated Mar. 23, 2017, for corresponding U.S. Appl. No. 15/268,071.

(Continued)

*Primary Examiner* — Yate K Cutliff
(74) *Attorney, Agent, or Firm* — Graham Curtin, P.A.

(57) ABSTRACT

There is disclosed a process for producing taurine from ammonium isethionate by the ammonolysis of alkali isethionate in the presence of alkali ditaurinate or alkali tritaurinate, or their mixture, to inhibit the formation of byproducts and to continuously convert the byproducts of the ammonolysis reaction to alkali taurinate. Alkali taurinate is reacted with ammonium isethionate to obtain taurine and to regenerate alkali isethionate. The production yield is increased to from 90% to nearly quantitative. The ammonolysis reaction is catalyzed by alkali salts of hydroxide, sulfate, sulfite, phosphate, or carbonate.

9 Claims, 1 Drawing Sheet

(56) References Cited

U.S. PATENT DOCUMENTS

| | | | |
|---|---|---|---|
| 9,593,076 | B2 | 3/2017 | Hu |
| 9,598,357 | B1 | 3/2017 | Hu |
| 2014/0121405 | A1* | 5/2014 | Chen .................... C07C 303/18 562/104 |

FOREIGN PATENT DOCUMENTS

| | | | |
|---|---|---|---|
| CN | 101508658 | A | 8/2009 |
| CN | 101508659 | A | 8/2009 |
| CN | 101717353 | A | 6/2010 |
| CN | 104945289 | A | 9/2015 |
| CN | 105732440 | A | 7/2016 |
| CN | 106008280 | A | 10/2016 |
| DE | 219023 | A3 | 2/1985 |
| WO | 0177071 | A1 | 10/2001 |

OTHER PUBLICATIONS

USPTO Final Office Action dated Jun. 9, 2017, for corresponding U.S. Appl. No. 15/268,071.

\* cited by examiner

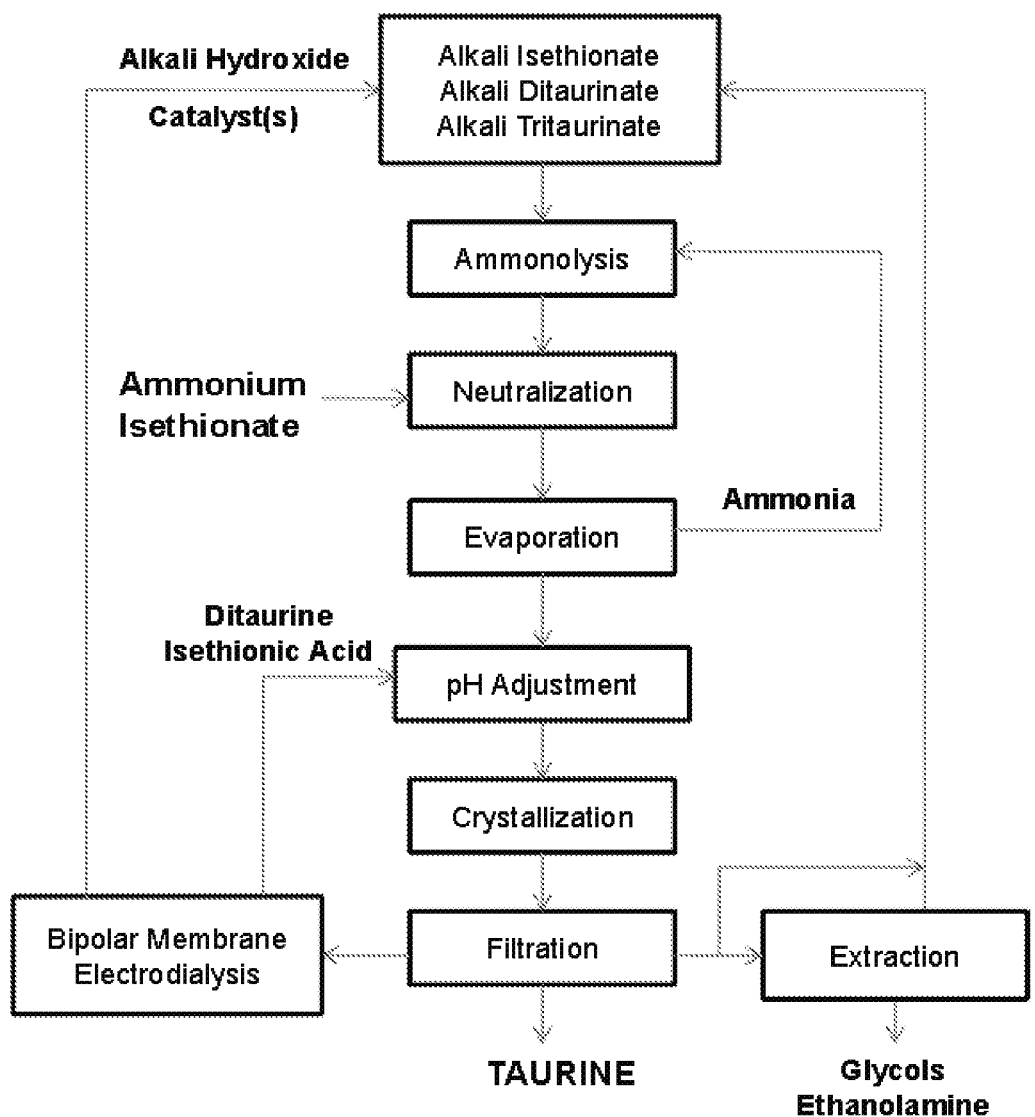

CYCLIC PROCESS FOR PRODUCING TAURINE

CROSS REFERENCE TO RELATED APPLICATION

This application is a continuation-in-part of application Ser. No. 15/268,071, filed on Sep. 16, 2016, which is incorporated herein by reference.

TECHNICAL FIELD

The present invention relates to a cyclic process for the production of taurine from ammonium isethionate in a high overall yield (i.e., greater than 90% to nearly quantitative) by carrying out the ammonolysis reaction of alkali isethionate to alkali taurinate in the presence of a mixture of alkali ditaurinate and alkali tritaurinate, followed by reacting with ammonium isethionate.

BACKGROUND OF THE INVENTION

Taurine can be referred to as 2-aminoethanesulfonic acid and is one of the amino sulfonic acids found in the tissues of many animals. Taurine is an extremely useful compound with beneficial pharmacological effects, such as detoxification, fatigue-relief, and nourishing and tonifying effects. As a result, taurine finds wide applications as an essential ingredient for human and animal nutrition.

Taurine is currently produced in an amount of over 50,000 tons per year from either ethylene oxide or monoethanolamine. At the present time, most taurine is produced from ethylene oxide, following a three-step process: (1) the addition reaction of ethylene oxide with sodium bisulfite to yield sodium isethionate; (2) the ammonolysis of sodium isethionate to yield sodium taurinate; (3) the neutralization with an acid, i.e., hydrochloric acid and, preferably, sulfuric acid, to generate taurine and inorganic salts.

Although the ethylene oxide process is well established and widely practiced in commercial production, the overall yield is not very high, less than 80%. Moreover, the process generates a large waste stream that is increasingly difficult to dispose of.

The first stage of the ethylene oxide process, the addition reaction of ethylene oxide with sodium bisulfite, is known to yield sodium isethionate in high yield, practically quantitative, as disclosed in U.S. Pat. No. 2,820,818 under described conditions.

Therefore, the problems encountered in the production of taurine from the ethylene oxide process arise from the ammonolysis of sodium isethionate and from the separation of taurine from sodium sulfate U.S. Pat. No. 1,932,907 discloses that sodium taurinate is obtained in a yield of 80%, when sodium isethionate undergoes ammonolysis reaction in a molar ratio of 1:6.8 for 2 hours at 240 to 250° C. U.S. Pat. No. 1,999,614 describes the use of catalysts, i.e., sodium sulfate, sodium sulfite, and sodium carbonate, in the ammonolysis reaction. A mixture of sodium taurinate and sodium ditaurinate is obtained in a yield as high as 97%. However, the percentage for sodium taurinate and sodium ditaurinate in the mixture is not specified.

DD219023 describes detailed results on the product distribution of the ammonolysis reaction of sodium isethionate. When sodium isethionate undergoes the ammonolysis reaction with 25% aqueous ammonia in a molar ratio of 1:9 at about 280° C. for 45 minutes in the presence of sodium sulfate and sodium hydroxide as catalyst, the reaction products comprise 71% of sodium taurinate and 29% of sodium di- and tritaurinate.

WO01/77071 is directed to a process for the preparation of ditaurine by heating an aqueous solution of sodium taurinate at a temperature of 210° C. in the presence of a reaction medium. A mixture of sodium taurinate and sodium ditaurinate is obtained.

It is therefore concluded from the foregoing references that the ammonolysis of sodium isethionate invariably yields a mixture of sodium taurinate, sodium ditaurinate, and sodium tritaurinate. The percentage yield of sodium taurinate has not been more than 80%.

In order to obtain taurine from sodium taurinate, U.S. Pat. No. 2,693,488 discloses a method of using ion exchange resins involving a strongly acid ion exchange resin in hydrogen form, and then an anion exchange resin in basic form. This process is complicated and requires the use of a large quantity of acid and base to regenerate the ion exchange resins in each production cycle.

On the other hand, CN101508657, CN101508658, CN101508659, and CN101486669 describe a method of using sulfuric acid to neutralize sodium taurinate to obtain a solution of taurine and sodium sulfate. Crude taurine is easily obtained by filtration from a crystalline suspension of taurine after cooling. However, the waste mother liquor still contains taurine, sodium sulfate, and other unspecified organic impurities, which are identified as a mixture of sodium ditaurinate and sodium tritaurinate.

U.S. Pat. No. 9,428,450 and U.S. Pat. No. 9,428,451 overcome some of the problems in the known ethylene oxide process by converting the byproducts of the ammonolysis reaction of alkali isethionate, alkali ditaurinate and alkali tritaurinate, into alkali taurinate. The overall yield of the cyclic process for producing taurine from sodium isethionate is increased to from 85% to nearly quantitative.

U.S. Pat. No. 8,609,890 discloses a process of using isethionic acid or sulfur dioxide to neutralize alkali taurinate to producing taurine and to regenerate alkali isethionate. U.S. Pat. No. 9,108,907 further discloses a process of using isethionic acid prepared from ethanol to neutralize alkali taurinate to regenerate alkali isethionate. The aim is to reduce or eliminate the use of sulfuric acid as an acid agent in the production of taurine.

U.S. Pat. No. 9,061,976 discloses an integrated production scheme by using sulfur dioxide as an acid and by converting the byproducts of the ammonolysis reaction, alkali ditaurinate and alkali tritaurinate, to alkali taurinate. The overall production yield is increased to greater than 90% and alkali sulfate is eliminated from the production process. One drawback of this process is the use of gaseous sulfur dioxide, which imparts a slight smell on the product. Another significant drawback is that the taurine product from this process may contain trace amount of alkali sulfite which could be an allergen for certain people.

Copending U.S. Ser. No. 15/238,621 discloses a cyclic process for producing taurine from isethionic acid in a high overall yield of greater than 90% to nearly quantitative, while generating no inorganic salt as byproducts. However, the starting material, isethionic acid, is difficult to obtain commercially and is produced by a costly process of bipolar membrane electrodialysis of alkali isethionate.

CN 101717353A describes a process of preparing taurine by (1) reacting ethylene oxide with ammonium sulfite to yield ammonium isethionate and ammonia; (2) ammonolysis of the obtained product to ammonium taurinate; (3)

acidifying with sulfuric acid to afford taurine. However, repeated attempts fail to produce any taurine under disclosed conditions.

It is an object of the present invention to overcome the disadvantage of the known processes for the production of taurine and to provide, in addition, advantages, which will become apparent from the following description.

It is another object of the present invention to disclose a process for the production of taurine from ammonium isethionate in a high overall yield (i.e., greater than 90% to nearly quantitative) without generating any inorganic salt as byproduct.

The starting material, ammonium isethionate, can be readily and economically produced by reacting ethylene oxide with ammonium bisulfite according to prior art, e.g., U.S. Pat. No. 5,646,320 and U.S. Pat. No. 5,739,365.

According to the process of the present invention, a solution of alkali isethionate or regenerated alkali isethionate, alkali ditaurinate, and alkali tritaurinate is mixed with an excess ammonia and is subjected continuously to the ammonolysis reaction to form a mixture of alkali taurinate, alkali ditaurinate, and alkali tritaurinate, in the presence of one or more catalysts. After ammonium isethionate is added to the ammonolysis solution, excess ammonia is removed to obtain a crystalline suspension of taurine in a solution of alkali isethionate, alkali ditaurinate, and alkali tritaurinate. Upon the solid-liquid separation of taurine, the mother liquor is directly recycled to the ammonolysis step.

The advantage of using ammonium isethionate as a starting material becomes apparent in that no isolation of alkali salt as a byproduct is necessary after the separation of crystalline taurine from the mother liquor containing alkali isethionate, alkali ditaurinate, and alkali tritaurinate.

BRIEF DESCRIPTION OF THE DRAWING

The FIGURE illustrates one embodiment of a flowchart for producing taurine from ammonium Isethionate.

DESCRIPTION OF THE INVENTION

The present invention relates to a cyclic process for the production of taurine from ammonium isethionate in a high overall yield of greater than 90% to nearly quantitative without generating any inorganic salt as byproduct.

The starting material, ammonium isethionate is produced by reacting ethylene oxide with ammonium bisulfite according to the following equation:

Ammonium isethionate, produced in a solution, can be used directly for the production of taurine. Preferably, ammonium isethionate is purified by concentrating the solution to obtain crystalline materials. When solid ammonium isethionate is used in the production of taurine, the quality of taurine produced is improved and almost no purge of mother liquor is required from the cyclic process.

The process according to the present invention starts with mixing a solution of alkali isethionate or regenerated alkali isethionate, alkali ditaurinate, and alkali tritaurinate, with an excess of ammonia. The presence of alkali ditaurinate and alkali tritaurinate in the reaction solution inhibits the formation of byproducts, increases the production yield, and greatly reduces or eliminates the waste discharge from the production process. The alkali metals are lithium, sodium, or potassium.

The ammonolysis reaction is carried out at a temperature from 160° C. to 280° C. under the pressure from autogenous to 260 bars for 1 to 6 hours.

After the ammonolysis reaction, ammonium isethionate is added to the ammonolysis solution to react with alkali taurinates. After excess ammonia and the ammonia released from the reaction are dispelled from the reaction solution and reclaimed for reuse, the pH of the solution or crystalline suspension is adjusted with an acid to a range of pH 5 to 8. Upon concentrating and cooling, a crystalline suspension of taurine is obtained in a solution of alkali ditaurinate, alkali tritaurinate, and alkali isethionate. The taurine obtained shows no foul smell of ammonia.

The amount of ammonium isethionate in relation to alkali taurinate in the ammonolysis solution can be from 0.1 to 10 on the molar basis. Preferably, the molar ratio is from 0.5 to 1.5, more preferably from 0.9 to 1.1, and most preferably from 0.95 to 1.05. When the ratio is lower than the equivalent, the final pH after ammonia removal tends to be higher than 7 and more taurine will remain in the solution. When the ratio is greater than equivalent, the final pH is in the desirable range of 5 to 6, but additional alkali hydroxide will be consumed during the ammonolysis stage.

The reaction of alkali taurinate formed in the ammonolysis stage with ammonium isethionate proceeds according to the following equation:

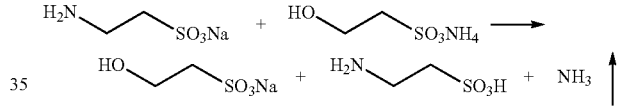

Removal of the excess ammonia and ammonia released from the above reaction can be effected by heating or by stripping with steam. After complete removal of ammonia, the strongly basic solution becomes neutral to yield a crystalline suspension of taurine in a solution of alkali isethionate, alkali ditaurinate, and alkali tritaurinate.

If the ammonia is not completely removed from the solution, the product will have a slight foul smell of ammonia. In this case, the final pH of the solution before crystallization or crystalline suspension of taurine can also be further neutralized with an acid or passed through an acidic ion exchanger to remove trace amount of free ammonia. The final pH is in the range of 4 to 9, preferably 5 to 8, more preferably 5.5 to 7.5, and most preferably 6.5 to 7.0. At higher pH than 7, a slight foul smell of ammonia is present in the isolated product of taurine. At a pH lower than 5, necessarily extra amount of acid is used in the process.

An acid can be selected from the group of sulfuric acid, hydrochloric acid, hydrobromic acid, nitric acid, phosphoric acid, organic carboxylic acid, and organic sulfonic acid. The acid is preferably isethionic acid, and more preferably, the mixed acids of isethionic acid and ditaurine, produced by bipolar membrane electrodialysis of the mother liquor containing alkali isethionate and alkali ditaurinate. The initial suspension is optionally concentrated, then cooled to crystallize taurine. Taurine is obtained by means of solid-liquid separation.

The amount of acid used to adjust the final pH of the solution or crystalline suspension depends on the amount of ammonium isethionate used to react with alkali taurinate. If ammonium isethionate is less than equal molar of alkali taurinate, then the solution after removal of ammonia is basic with a pH greater than 7. In general, the sum of acid needed and ammonium isethionate added is equal to or slightly more than the molar equivalent of alkali taurinates in the ammonolysis solution. It is therefore possible to adjust the ratio of ammonium isethionate and isethionic acid/ditaurine mixture, according to the availability the mixed acids produced from the bipolar membrane electrodialysis of the mother liquor containing alkali isethionate and alkali ditaurinate. As the mixed acid is produced in the bipolar membrane electrodialysis, it is therefore preferable to add less than equivalent amount of ammonium isethionate to react with alkali taurinates, with the balance from the mixed acid of isethionic acid and ditaurine.

An added advantage of the current process of using both less than equivalent ammonium isethionate and isethionic acid/ditaurine is the nearly complete removal of ammonia from the reaction solution at much higher pH. The alkaline pH of the solution helps to accelerate the removal of ammonia from the solution. After complete removal of ammonia, the pH of the solution or crystalline suspension is brought down with a solution of the mixed acids of isethionic acid and ditaurine.

After separation of taurine, the mother liquor, containing regenerated alkali isethionate, alkali ditaurinate, and alkali tritaurinate, is saturated with ammonia and is subjected to the ammonolysis reaction.

It becomes apparent that alkali in the reaction system is continuously recycled in the process and only ammonium isethionate is transformed to taurine. The net reaction of the cyclic process is:

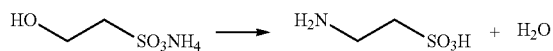

Useful and effective catalysts for the ammonolysis reaction are found among the alkali salts of hydroxide, carbonate, bicarbonate, hydrogen sulfate, sulfate, bisulfite, sulfite, nitrate, phosphate, chlorate, and perchlorate. Such salts are sodium hydroxide, lithium hydroxide, potassium hydroxide, lithium carbonate, lithium bicarbonate, sodium bicarbonate, sodium bicarbonate, potassium bicarbonate, lithium carbonate, sodium carbonate, potassium carbonate, lithium sulfate, sodium sulfate, potassium sulfate, lithium phosphate, sodium phosphate, potassium phosphate, lithium sulfite, sodium sulfite, and potassium sulfite.

The catalyst for the ammonolysis reaction of alkali isethionate in the presence of alkali ditaurinate and alkali tritaurinate can be one component or a combination of two or more components. Preferable catalysts are alkali hydroxides and the most preferable catalyst is sodium hydroxide.

The amount of the catalyst used is not limited, but is usually from 0.01 to 10 in molar ratio of the catalyst to alkali isethionate. The ratio is preferably in the range of 0.01 to 1, more preferably 0.1 to 0.5, most preferably 0.2 to 0.3. A suitable amount of catalyst can be selected by those skilled in the art for the ammonolysis reaction to complete in desired time.

As a catalyst, alkali hydroxide is introduced into the reaction system and additional ammonium isethionate is required to neutralize the strong base. The result is an increased accumulation of alkali in the cyclic process. It is thus preferable to generate the alkali hydroxide within the production unit as shown in the FIGURE a convenient way is to split alkali isethionate and alkali ditaurinate in the mother liquor into an acid component, a mixture of isethionic acid and ditaurine, and an alkali hydroxide component, by using bipolar membrane electrodialysis. The mixed acid solution of isethionic acid and ditaurine is used as an acid for neutralization and pH adjustment, while the alkali hydroxide produced is used as a catalyst for the ammonolysis reaction.

The proportion of mother liquor that goes through the electrodialysis process can be adjusted according to the need of alkali hydroxide as a catalyst for the ammonolysis reaction and the need of the acidic part for the neutralization and pH adjustment. The ratio is varied from 1% to 50%, preferably from 5 to 30%, most preferably from 10-20%.

The cyclic process according to the present invention affords taurine in a yield of greater than 90%, to nearly quantitative, and generates no waste other than byproducts of ethylene glycol and monoethanolamine, which are removed from the cyclic process by an extraction process as disclosed in the co-pending application.

The process according to the present invention can be carried out discontinuously, semi-continuously, and continuously.

EXAMPLES

The following examples illustrate the practice of this invention but are not intended to limit its scope.

Example 1

To a 2-L autoclave were added 1200 mL of 24% ammonia solution, 296 g of sodium isethionate, and 2 g of sodium hydroxide. The solution was heated to 260° C. for 2 hours under autogenous pressure. After cooling, 260.0 g of ammonium isethionate was added and ammonia was removed by boiling the solution to a temperature of 104° C. After cooling to 70° C., a solution of 65% isethionic acid was added to bring the pH to 6.5. After concentrating and cooling to room temperature, a suspension of crystalline taurine was obtained. Taurine was recovered by filtration and dried to 192.1 g. Taurine is recovered in a yield of 76.8%.

Example 2

To the mother liquor of Example 1 was added 340 g of gaseous ammonia and total volume was adjusted to 1500 mL with deionized water, followed by addition of 12.4 g of sodium hydroxide. The solution was placed in a 2-L autoclave and was subjected to ammonolysis reaction and treatment with ammonium isethionate and a mixture of isethionic acid and ditaurine as described in Example 1.

Taurine, 235.4 g after drying, was obtained in a yield of 94.1% on the molar basis of ammonium isethionate, isethionic acid, and ditaurine introduced into the reaction solution.

It will be understood that the foregoing examples, drawing, and explanation are for illustrative purposes only and that various modifications of the present invention will be self-evident to those skilled in the art. Such modifications are to be included within the spirit and purview of this application and the scope of the appended claims.

What is claimed is:

1. A cyclic process for producing taurine from ammonium isethionate, comprising:
   (a) adding ammonium isethionate to a solution of a mixture of alkali taurinate, alkali ditaurinate, and alkali tritaurinate to react with alkali taurinates;

(b) removing ammonia from (a) to obtain a solution or crystalline suspension of taurine in a solution of alkali isethionate, alkali ditaurinate, and alkali tritaurinate;

(c) adding art acid or an acidic ion exchanger to adjust the pH of the solution or crystalline suspension of step (b) to a range from 5 to 9;

(d) separating taurine by means of solid-liquid separation to provide a mother liquor containing alkali isethionate, alkali ditaurinate, and alkali tritaurinate; and (e) adding ammonia or ammonium hydroxide to the mother liquor of step (d) and subjecting the solution to an ammonolysis reaction to produce a solution of a mixture of alkali taurinate, alkali ditaurinate, and alkali tritaurinate.

2. The process according to claim 1, wherein the acid is selected from the group of sulfuric acid, hydrochloric acid, hydrobromic acid, nitric acid, phosphoric acid, organic carboxylic acids, alkyl sulfonic acids, and aryl sulfonic acids.

3. The process according to claim 1, wherein the acid is isethionic acid.

4. The process according to claim 1, herein the acid is a mixture of isethionic acid, ditaurine, and tritaurine.

5. The process according to claim 1, wherein the acid is produced by a process of bipolar membrane electrodialysis of a solution of alkali isethionate or a mixture of alkali isethionate, alkali ditaurinate, and alkali tritaurinate.

6. The process according to claim 1, wherein an acid is used to adjust the pH of taurine solution or crystalline suspension to a range of 6 to 8.

7. The process according to claim 1, wherein the taurine solution is passed through a bed of acidic ion exchanger.

8. The process according to claim 1, wherein the yield of taurine from ammonium isethionate is from 90% to nearly quantitative.

9. The process according to claim 1, wherein the alkali metals are lithium, sodium, or potassium.

* * * * *

UNITED STATES PATENT AND TRADEMARK OFFICE
CERTIFICATE OF CORRECTION

PATENT NO.        : 9,815,778 B1
APPLICATION NO.   : 15/366798
DATED             : November 14, 2017
INVENTOR(S)       : Songzhou Hu It is certified that error appears in the above-identified patent and that said Letters Patent is hereby corrected as shown below:

In the Claims

Column 7, Line 4 (Claim 1. ( c )):
Change from "art acid" to -- an acid --.

Column 8, Line 3 (Claim 4.):
Change from "herein" to -- wherein --.

Signed and Sealed this
Twentieth Day of February, 2018

Andrei Iancu
*Director of the United States Patent and Trademark Office*